(12) United States Patent
Iwama

(10) Patent No.: US 9,354,313 B2
(45) Date of Patent: May 31, 2016

(54) ULTRASOUND DIAGNOSTIC APPARATUS AND METHOD FOR ACQUIRING ULTRASOUND DATA

(75) Inventor: Nobuyuki Iwama, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 2327 days.

(21) Appl. No.: 12/054,184

(22) Filed: Mar. 24, 2008

(65) Prior Publication Data

US 2008/0234585 A1 Sep. 25, 2008

(30) Foreign Application Priority Data

Mar. 22, 2007 (JP) .................................. P2007-74345

(51) Int. Cl.
*A61B 8/00* (2006.01)
*G01S 15/89* (2006.01)
*G10K 11/34* (2006.01)

(52) U.S. Cl.
CPC ......... *G01S 15/8927* (2013.01); *G01S 15/8925* (2013.01); *G10K 11/346* (2013.01); *A61B 8/00* (2013.01)

(58) Field of Classification Search
USPC ........................... 600/447, 407, 444, 446, 463
See application file for complete search history.

(56) References Cited

U.S. PATENT DOCUMENTS

| | | | |
|---|---|---|---|
| 2005/0277853 A1* | 12/2005 | Mast et al. ........................ 601/2 |
| 2006/0058661 A1* | 3/2006 | Hirama ......................... 600/437 |
| 2008/0009741 A1* | 1/2008 | Hyuga ........................... 600/459 |
| 2008/0154133 A1* | 6/2008 | Shiki ............................. 600/443 |
| 2008/0242988 A1* | 10/2008 | Yoshida et al. ................. 600/443 |
| 2009/0018441 A1* | 1/2009 | Willsie et al. ................. 600/437 |
| 2009/0140810 A1* | 6/2009 | Kim et al. ...................... 330/254 |
| 2009/0171214 A1* | 7/2009 | Kim et al. ...................... 600/447 |
| 2009/0198134 A1* | 8/2009 | Hashimoto et al. ............ 600/443 |
| 2009/0230823 A1* | 9/2009 | Kushculey et al. ............ 310/366 |
| 2009/0251461 A1* | 10/2009 | Sasaki et al. ................... 345/419 |
| 2010/0076352 A1* | 3/2010 | Kim et al. ......................... 601/2 |
| 2010/0312150 A1* | 12/2010 | Mast et al. ........................ 601/2 |

FOREIGN PATENT DOCUMENTS

| | | |
|---|---|---|
| JP | 2005-34634 | 2/2005 |
| JP | 2005-342194 | 12/2005 |

* cited by examiner

*Primary Examiner* — Amanda Lauritzen Moher
*Assistant Examiner* — Serkan Akar
(74) *Attorney, Agent, or Firm* — Oblon, McClelland, Maier & Neustadt, L.L.P.

(57) ABSTRACT

An ultrasound diagnostic apparatus including oscillation elements configured to transmit toward and receive from a region of a subject, a receiving delay setting unit configured to divide the oscillation elements into oscillation element groups and set a common delay to oscillation elements included in each of the oscillation element groups in accordance with an imaging condition, an adding unit configured to add received signals transmitted from the oscillation elements in accordance with the delay set by the received delay setting unit, and an image generating unit configured to generate image data in accordance with received signal added by adding unit.

20 Claims, 6 Drawing Sheets

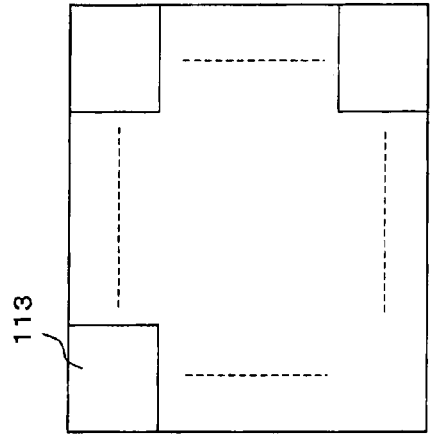
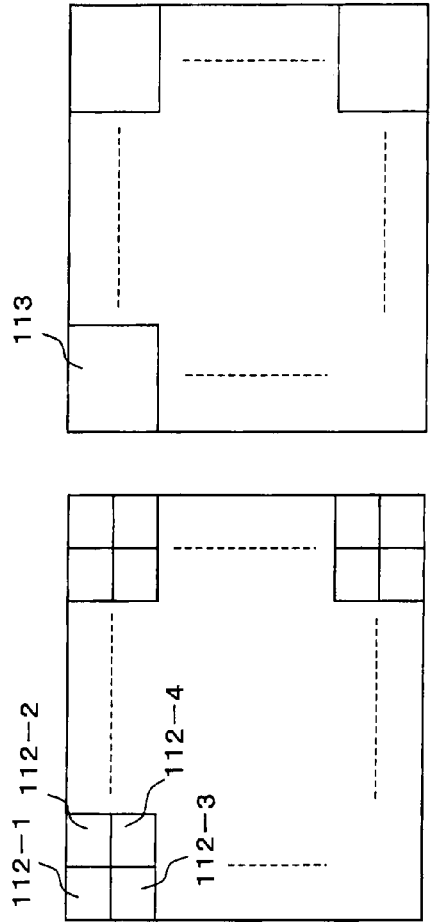
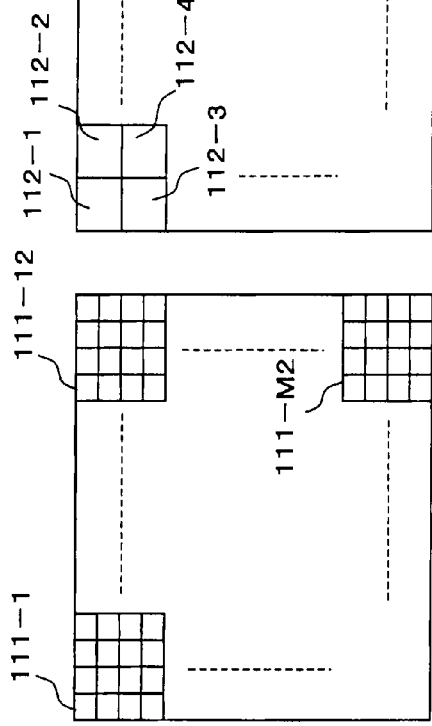

ULTRASOUND DIAGNOSTIC APPARATUS AND METHOD FOR ACQUIRING ULTRASOUND DATA

CROSS REFERENCE TO RELATED APPLICATIONS

This application is based upon and claims the benefit of priority from prior Japanese Patent Application No. 2007-74345, filed on Mar. 22, 2007, the entire contents of which are incorporated herein by reference.

BACKGROUND OF THE INVENTION

An ultrasound diagnostic apparatus transmits ultrasound wave generated by array transducers in an ultrasound probe to a subject and displays images based on ultrasound wave reflected from acoustic impedance boundary surfaces. An ultrasound diagnostic apparatus is extensively used in diagnosis of function and conformation of organs because it is easy to acquire diagnostic images.

In the most popular scan technique of the ultrasound diagnostic apparatus, array transducers arranged in a row are driven electrically and ultrasound images are acquired. Recently, a 2-dimensional array probe or a mechanical oscillation 1-dimension array probe can acquire 3-dimensional image data in that it is now possible to obtain volume rendering images or MPR (multi plane reconstruction) images by reconstruction of the 3 dimensional image data. In the ultrasound diagnosis of a heart or a circulatory organ, the 2-dimensional array probe is often used for acquiring real-time 3-dimensional image data.

The 2-dimensional array probe has 2-dimensionally arrayed oscillation elements on a head part of the probe. The number of the oscillation elements (M0) requires several hundredfold the number of M0 in the 1-dimensional array probe. Therefore, for adding received signals from M0 channels, a cable connecting each of the 2-D oscillation elements in the probe and phase match adding unit in the apparatus body becomes very heavy and can seriously impair handing of the probe.

To solve the above-mentioned problem, Japanese patent disclosure (kokai) No 2005-342194 discloses a method in which first phase match adding units for M2 channels (M2<M0) are provided in the probe and M0 oscillation elements are sectionalized in M2 sub-arrays (each of the sub-arrays includes M1 oscillation elements (M1=M0/M2)). The received signals from M1 elements of each sub array are added in the first phase match adding unit and the received signals of M0 channels are bundled together in received signals of M2 channels.

In this manner, the bundled received signals of M2 channels are transmitted to a second phase match adding unit in the apparatus body by a cable for M2 channels. This second phase match adding unit bundles the received signals of M2 channels in 1 channel received signal. In other words, two adding steps at both the probe and the apparatus body decrease the number of channels into the cable and result in improved handling ability of the probe.

By the way, by the electronic scan of the ultrasound diagnostic apparatus that receives ultrasound from a certain direction by controlling time delay or phase delay of return signal received by arrayed oscillation elements, especially in the case that a number of oscillation elements per unit area is a few, the larger the angle of ultrasound transmitting and receiving relative to the normal line is, the lower is the sensitivity of receiving and image quality, resulting in artifacts caused from increased side lobes.

In addition, in the case that the first phase match adding units are provided in the ultrasound probe, delay signals for controlling time delay or phase delay of the first phase match adding units are normally supplied from the apparatus body in chronological order. Therefore, too many oscillation elements arrayed on the probe head make transfer time of the delay signals for the many oscillation elements too long.

For example, a case that 2304 oscillation elements on an X-Y surface composed of 48 elements along each of the X and Y directions is explained below. In a case that delay data for 2304 oscillation elements is serially transmitted at a 80 Hz repetition frequency from apparatus body, more than a 30μ sec transfer time is needed and the repetition cycle (rate cycle) of 3-dimensional ultrasound transmitting and receiving must be increased to accommodate the transfer time. In other words, when the first phase match adding unit is provided in the apparatus body, because of the transfer time of a large amount of delay data to the first phase match adding unit, there arises a problem that time resolution of data acquisition and displaying are deteriorated.

On the other hand, to solve the problem, it is possible to increase repetition frequency of transfer or adopt parallel transfer. However these solutions further complicate circuit structure and increase power consumption.

BRIEF SUMMARY OF THE INVENTION

According to one aspect of the present invention, there is provided an ultrasound diagnostic apparatus including an ultrasound probe including oscillation elements configured to transmit toward and receive from a region of a subject, a receiving delay setting unit configured to divide the oscillation elements into oscillation element groups and set a common delay to oscillation elements included in each of the oscillation element groups in accordance with an imaging condition, an adding unit configured to add received signals transmitted from the oscillation elements in accordance with the delay set by the received delay setting unit, and an image generating unit configured to generate image data in accordance with received signal added by adding unit.

According to another aspect of the present invention there is provided a method of acquiring ultrasound data, including transmitting ultrasound signals toward and receiving ultrasound signals from a region of a subject using oscillation elements provided in an ultrasound probe, dividing the oscillation elements into oscillation element groups, setting a common delay to oscillation elements included in each of the oscillation element groups in accordance with a imaging condition, adding received signals transmitted from the oscillation elements in accordance with the delay set by the received delay setting unit, and generating image data in accordance with received signal added by adding unit.

BRIEF DESCRIPTION OF THE SEVERAL VIEWS OF THE DRAWING

A more complete appreciation of the invention and many of the attendant advantages thereof will be readily obtained as the same becomes better understood by reference to the following detailed description when considered in connection with the accompanying drawings, wherein:

FIGS. 4(a), 4(b) 4(c) and 4(d) are frame formats showing the variety of section manner for second oscillation element groups of an exemplary embodiment of the ultrasound diagnostic apparatus of the invention.

DETAILED DESCRIPTION OF THE PREFERRED EMBODIMENTS

Figure 1:
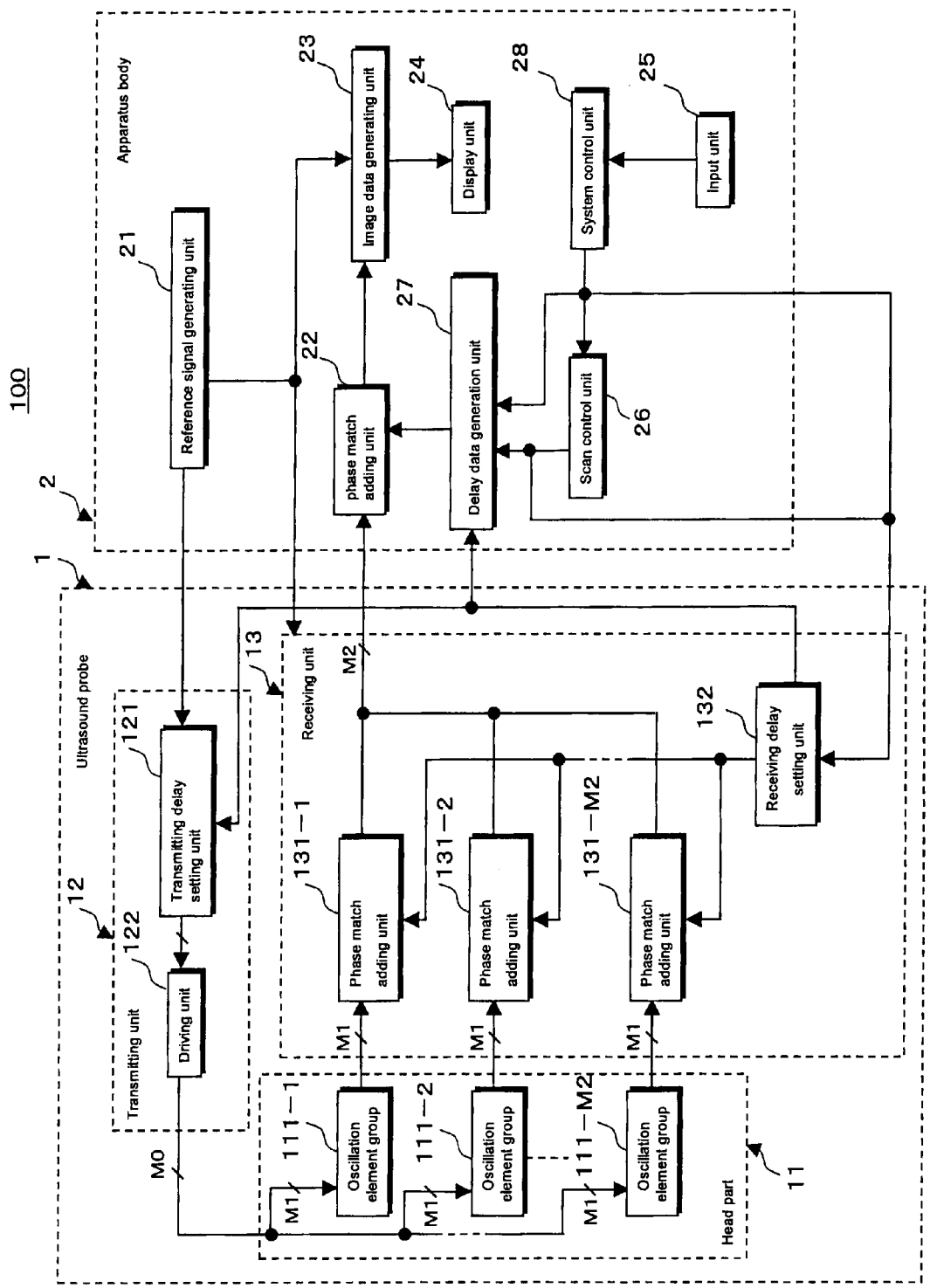
FIG. 1 is a block diagram showing whole components of an exemplary embodiment of the ultrasound diagnostic apparatus of the invention.

Referring now to the drawings, wherein like reference numerals refer to the same or corresponding parts in the several views, an exemplary embodiment of the present invention is next explained. First phase match adding units composed of M2 channels (M2=144) are provided in an ultrasound probe. M0 (M0=2304) oscillation elements two-dimensional arrayed on a head of the ultrasound probe are divided into same number of the first phase match adding units. When the received signal of M0 channels from the M1 oscillation elements in each of first oscillation element groups is bunched into M2 channels by adding in the first phase match adding unit, the M1 oscillation elements of each of the first oscillation elements groups are further divided into second oscillation element groups in accordance with image mode or condition of ultrasound data acquisition (imaging condition) and received signals from one second oscillation element group are gave delay in common.

In the other words, common setting of receiving signals from oscillation elements in each of the second oscillation element groups enables transfer time to decrease and enables time resolution of acquisition of image data to be advanced by decrease of amount of delay data to be transmitted from apparatus body.

An ultrasound apparatus indicated in FIG. 1 has an ultrasound probe 1 and an apparatus body 2. The ultrasound probe 1 has oscillation elements in its top and transmits and receives ultrasound. The apparatus body 2 generates and displays image data on the basis of received signal from the oscillation elements.

The ultrasound probe 1 also has a head part 11, transmitting unit 12 and receiving unit 13. The M0 oscillation elements are provided in the head part 11. The transmitting unit 12 generates driving signals and supplies the signals to the M0 (M0=2304) oscillation elements for transmitting ultrasound waves to a subject. The receiving unit 13 bunches M0 channel receiving signals into M2 (M2=144) channel receiving signals by phase match addition of M1 (M1=16) channels received signals. The M1 (M1=16) channels received signals are acquired from oscillation elements belonging to first oscillation elements 111-1 to 111-M2 wholly composing M0 oscillation elements.

Figure 2:
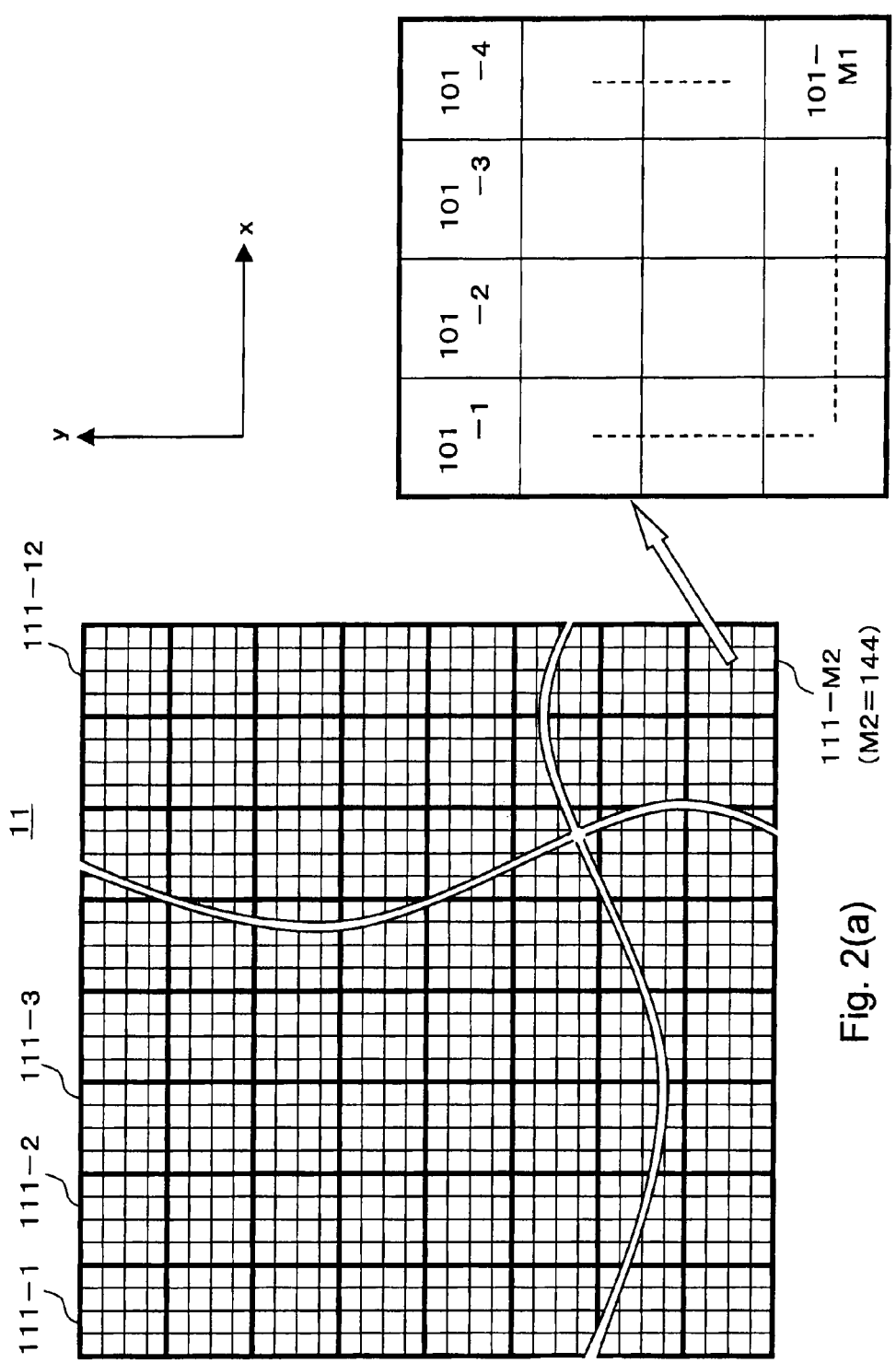
FIG. 2 is a frame format showing a section manner of oscillation elements of an exemplary embodiment of the ultrasound diagnostic apparatus of the invention.

M0 oscillation elements 2-dimensionally arrayed on the head part 11 and the first oscillation element groups 111-1 to 111-M2 each have M1 oscillation elements as described below with reference to FIGS. 2(a) and 2(b) shows the head part 11 in which the M0 oscillation elements are 2-dimensionally arrayed along X-Y directions. 48 oscillation elements are arrayed along one direction of X and Y. These ultrasound elements are divided into the M2 first oscillation elements groups 111-1, 111-2, 111-3 ... 111-M2 each having 4 oscillation elements along both X and Y directions. Each of the first oscillation elements groups 111-1 to 111-M2 is composed from M1 oscillation elements 101-1, 101-2, 101-3 ... 101-M1 as shown in FIG. 2 (b).

Next, a transmitting unit 12 has a transmitting delay setting unit 121 and a driving unit 122. The transmitting delay setting unit 121 generates timing pulses including information of delay time for focusing the ultrasound wave at predetermined depth and delay time for transmitting ultrasound to predetermined directions on the basis of a reference signal supplied from a reference signal generation unit 21. The driving unit 122 generates a driving signal for driving the oscillation elements and transmits ultrasound wave on the basis of above mentioned timing pulse.

On the other hand, the receiving unit 13 has M2 first phase match adding units 131-1 to 131-M2 and receiving delay setting unit 132. Each first phase match adding unit 131-1 to 131-M2 sets delays for focusing received ultrasound signals from a predetermined depth and delays for directionality of a predetermined direction, and then the first phase match adding unit bundling the delayed signals to one channel receiving signal.

Figure 3:
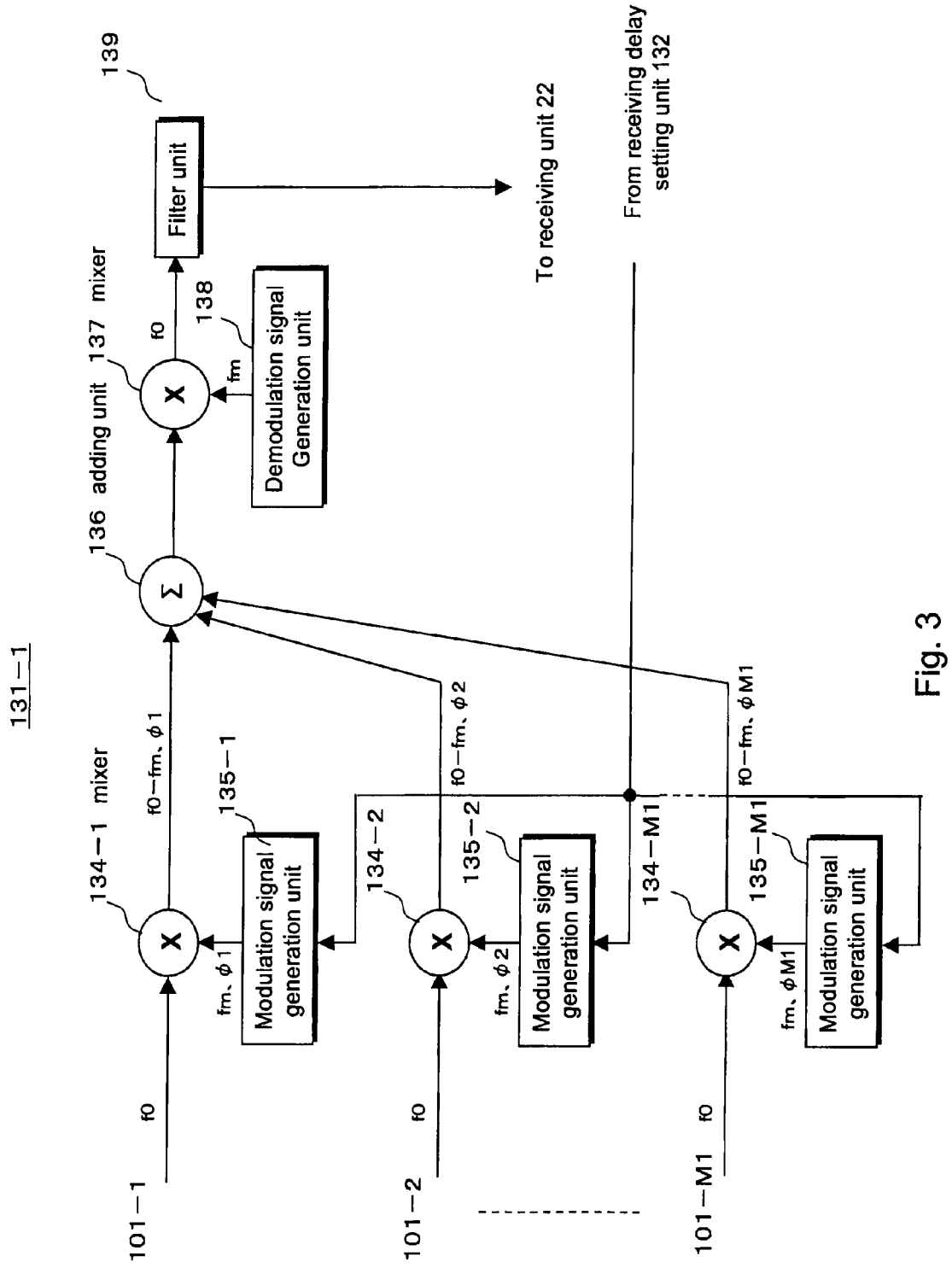
FIG. 3 is a block diagram showing components of a first phase match adding unit of an exemplary embodiment of the ultrasound diagnostic apparatus of the invention.

The phase match adding unit includes M1 channels mixers 134-1 to 134-M1 and modulation signal generation units 135-1 to 135-M1 and an adding unit 136, a mixer 137, a demodulation signal generation unit 138 and a filter unit 139 as shown in FIG. 3.

The mixers 134-1 to 134-M1 and the modulated signal generation units 135-1 to 135-M1 demodulate received signals of M1 channels supplied from the first oscillation element groups into a predetermined frequency provide the receiving signals predetermined phase delay on the basis of delay data set by below mentioned receiving delay setting unit 135 for oscillation elements 101-1 to 101-M1.

For example, in the case that a receiving signal having f0 center frequency is supplied from the oscillation 101-1 of the first oscillation elements group 111-1 to the mixer 134-1 and a modulation signal having fm frequency phase delay φ1 is supplied from modulation signal generation unit 135-1 on the basis of delay data supplied from receiving delay setting unit 132, the mixer 134-1 generates a received signal having f0-fm center frequency and phase delay φ1 by multiplication of the above mentioned receiving signal with the modulation signal.

In the same manner, each of mixers 134-2 to 134-M1 generates receiving signals having f0-fm center frequency and phase delay φ2 to φM1 by multiplication of supplied receiving signal from oscillation elements 101-2 to 101-M1 of the first oscillation group 111-1 and the modulation signal including fm frequency and phase delay φ2 to φM1 supplied from the modulation signal generation unit 135-2 to 135-M1.

Next, M1 channel receiving signals having f0-fm center frequency and phase delay φ1 to φM1 are phase matched and added and the phase matched and added signals having f0-fm center frequency are converted to phase matched and added receiving signal having f0 center frequency in the mixer 137 by multiplication with demodulation signal of fm frequency supplied from the demodulating signal generation unit 138.

In addition, it is explained above that a receiving signal having f0-fm center frequency is generated by multiplication in the mixers 134-1 to 134-M1. However, receiving signal having f0+fm center frequency is generated and not only receiving signal having f0 center frequency but also receiving signal having f0+2fm and f0−2fm center frequency is generated in the adding of the mixer 137. The filter unit 139 of the first phase matching and adding unit 131-1 eliminates such unexpected frequency component by filter processing and extracts receiving signal having f0 center frequency.

As noted above, the first phase matching and adding unit 131 bundles M1 channel receiving signal from the first oscillation elements group 111 into 1 channel receiving signal by phase matching and adding. In other words, M0 channel receiving signals acquired from M0 oscillation elements two-dimensionally arrayed in the head part 11 are bundled into a M2 channel receiving signal by adding signals corresponding to the number of elements of the first oscillation element group.

In addition, the ideal manner of delay setting of received signals is delaying both the envelope and phase of received signals, but where the delay time between neighboring oscillation elements is relatively small, only phase delaying enables the same accurate delay setting as the above ideal manner.

Returning to FIG. 1, the receiving delay setting unit 132 of the receiving unit 13 dividing the oscillation elements 101-1 to 101-m1 of each of the first oscillation elements 111-1 to 111-M2 into a second oscillation elements group on the basis of the imaging conditions (imaging mode and ultrasound data acquisition condition and so on) supplied from a system control unit 28. Next, on the basis of the division information, the receiving delay setting unit 132 sets delay data to the first phase match adding unit 131-1 to 131-M2, the delay data is generated by a below mentioned delay data generating unit 27 for each of the second oscillation elements group. The same delay data is set for oscillation elements belonging to same second oscillation element group.

Next, the method of setting delay data by receiving delay setting unit 132 is further explained with reference to FIG. 4 and FIG. 5.

M0 (M0=2304) oscillation elements 2-dimensionally arrayed in the head part 11 are divided into M2 (M2=144). The first oscillation elements groups 111-1 to 111-m2 have already been mentioned with the reference to FIG. 2. Each of the first oscillation elements groups 111-1 to 111-m2 is composed from M1 (M1=16) oscillation elements 101-1, 101-2, 101-3 . . . 101-M1. The receiving delay setting unit 132 in the receiving unit 13 divides the oscillation elements 101-1 to 101-M1 in each of the first oscillation element groups 111-1 to 111-M2 into the second oscillation element groups having predetermined size on the basis of above mentioned imaging conditions.

FIG. 4 shows a concrete example of the second oscillation element groups shaped in each of the first oscillation element group 111-1 to 111-M2. FIG. 4(a) shows an example not to shape the second oscillation element group in each of the first oscillation element group 111-1 to 111-M2. FIG. 4(b) shows an example of shaping four second oscillation element groups in each first oscillation element group 111-1 to 111-M2. FIG. 4(c) shows an example of shaping one second oscillation element group in each first oscillation element group 111-1 to 111-M2.

For example, if the second oscillation elements group 112-1 to 112-4 is shaped from the first oscillation elements group 111-1 as shown in FIG. 4(b), the receiving delay setting unit 132 sequentially receives four kinds of delay data Dd-1 to Dd-4 corresponding to the shaped second oscillation elements group 112-1 to 112-4 from the delay data generation unit 27 in the apparatus body 2. Next, receiving delay setting unit 132 supplies the delay data Dd-1 to the modulation signal generation units 135-1, 135-2, 135-5 and 135-6 of the first phase match adding unit 131-1 corresponding to the oscillation elements 101-1, 101-2, 101-5 and 101-6 of the second oscillation element group 112-1. Each modulation signal generation unit 135-1, 135-2, 135-5 and 135-6 then generates a modulation signal having phase delay according to the received delay data Dd-1.

Furthermore, receiving delay setting unit 132 supplies the delay data Dd-2 to the modulation signal generation units 135-3, 135-4, 135-7 and 135-8 of the first phase match adding unit 131-1 corresponding to the oscillation elements 101-3, 101-4, 101-7 and 101-8 of the second oscillation element group 112-2. The receiving delay setting unit 132 further supplies the delay data Dd-3 to the modulation signal generation unit 135-9, 135-10, 135-13 and 135-14 of the first phase match adding unit 131-1 corresponding to the oscillation elements 101-9, 101-10, 101-13 and 101-14 of the second oscillation element group 112-3. The receiving delay setting unit 132 further supplies the delay data Dd-3 to the modulation signal generation unit 135-11, 135-12, 135-15 and 135-16 of the first phase match adding unit 131-1 corresponding to the oscillation elements 101-11, 101-12, 101-15 and 101-16 of the second oscillation element group 112-4. Each modulation signal generation unit 135 receiving the delay data Dd-2 to Dd-4 generates a modulation signal having phase delay according to the received delay data Dd-2 to Dd-4.

In the same manner as above noted, in the first phase match adding unit 131-2 to 131-M2 corresponding to the first oscillation element group 111-2 to 111-M2, according to the unit of the second oscillation element group, setting of delay data and generation of modulation signal having a phase delay based on the delay data are executed.

As mentioned above, by setting the same delay for the second oscillation element group shaped by dividing of the first oscillation element 111-1 to 111-M2, the amount of delay data supplied from delay data generation unit 27 in the apparatus body 2 is decreased. Therefore this decreases the transfer time of the delay data. For example, the time required in the case that the second oscillation element group is not shaped as in FIG. 4(a) is 4 times as long as the case shown in FIG. 4(b) and is 16 times as long as the case shown in FIG. 4(c).

Figure 5B:
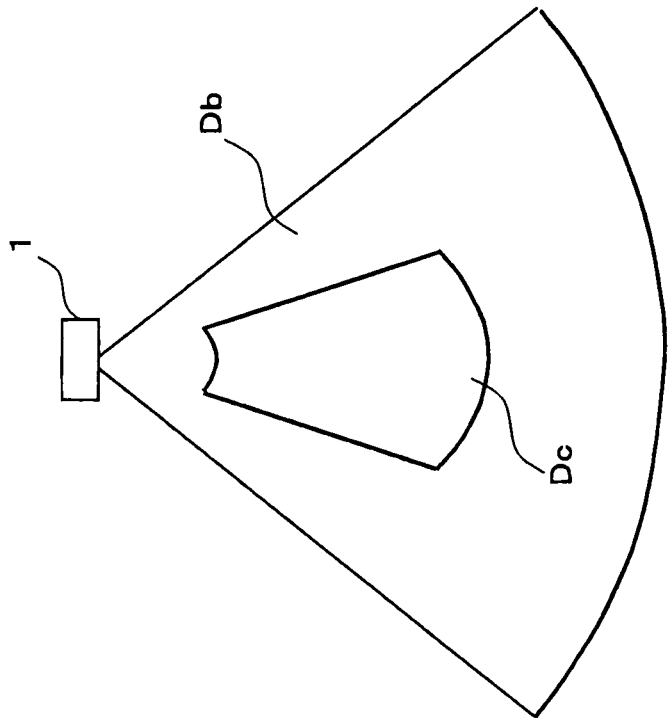
FIGS. 5(a) and 5(b) are frame formats showing scan region of an exemplary embodiment of the ultrasound diagnostic apparatus of the invention.
Figure 5A:
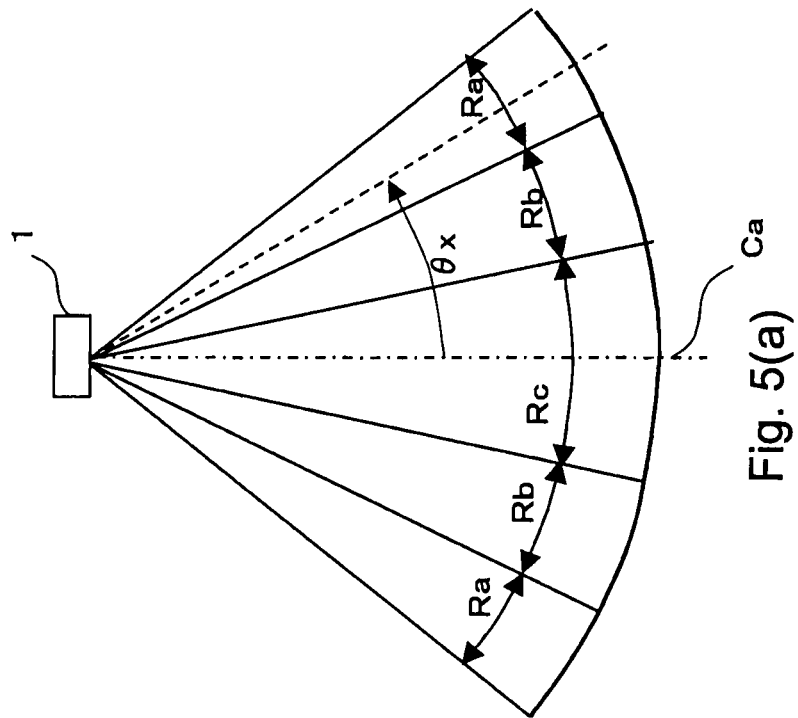

FIGS. 5(a) and 5(b) show a transmitting and receiving range of sector scan. For example, in the case that sector scan is executed from the ultrasound probe 1 as shown in FIG. 5(a), when the end region, where transmitting and receiving angle θx to normal line of oscillation elements arrayed plane is large, is scanned, because the difference of the delay time or phase between received signals received from the oscillation elements 101-1 to 101-M1 is also large, independent delay settings for the phase match adding unit 131-1 to 131-M2 corresponding to these oscillation elements are required.

On the other hand, when the center region, where the transmitting and receiving angle θx is small, is scanned, because the difference of the delay time or phase between received signals received from the oscillation elements 101-1 to 101-M1 is also small, a common delay setting for the phase match adding unit 131-1 to 131-M2 corresponding to these oscillation elements can be executed.

FIG. 5(b) shows a B mode image data Db and color Doppler image data Dc. Normally, for B mode imaging, high spatial resolution is required for shape diagnosis of biomedical tissue; and for color Doppler imaging, high time resolution is required for function diagnosis of circulation organs and so on. In that case, the receiving delay setting unit 132 sets a smaller number for the second oscillation element groups for color Doppler than the number for B mode imaging so that high space resolution B mode images and high time resolution color Doppler images can be acquired simultaneously or independently. Also, if below mentioned clutter noise contributing to side lobe can not be tolerated, the number of the second oscillation element groups for the color Doppler image may be set larger than the number for B mode imaging.

Furthermore, a number of the second oscillation element group can be set according to the frequency of transmitting ultrasound wave. For example, by setting a larger number for the second oscillation element groups for transmitting high ultrasound frequency, high quality image data can be obtained so that side lobe or nonuniformity of sensibility is stably decreased.

Returning to FIG. 1, the apparatus body 2 includes a reference pulse generation unit 21, a second phase match adding unit 22, an image data generation unit 23, a display 24, an input unit 25, a scan control unit 26, a delay data generation unit 27 and system control unit 28. The reference pulse generation unit 21 generates a reference signal having a predetermined frequency. The second phase match adding unit 22 bundles M2 channel receiving signals supplied from the receiving unit 13 into a 1 channel receiving signal by phase match adding. The image data generation unit 23 generates image data, such as B mode image data or color Doppler image data and so on, on the basis of receiving signals output from the second phase match adding unit 22. The display 24 displays the image data. An operator can input kinds of command signals, such as setting of acquiring condition of ultrasound data, subject information, image mode, display condition, by the input unit 25. The scan control unit 26 controls transmitting and receiving direction (scan direction), scan order and so on the basis of control signal from the system control unit 28. The delay data generation unit 27 generates delay data for the first phase match adding units 131-1 to 131-M2 and the second phase matching unit 22 on the basis of scan information supplied from the scan control unit 26, the imaging condition supplied from the system control unit 28 and the setting information of the second oscillation element group supplied from the receiving delay setting unit 132 of the receiving part 13. The system control unit 28 totally controls the ultrasound probe 1 and each above mentioned unit provided in the apparatus body 2.

Figure 6:
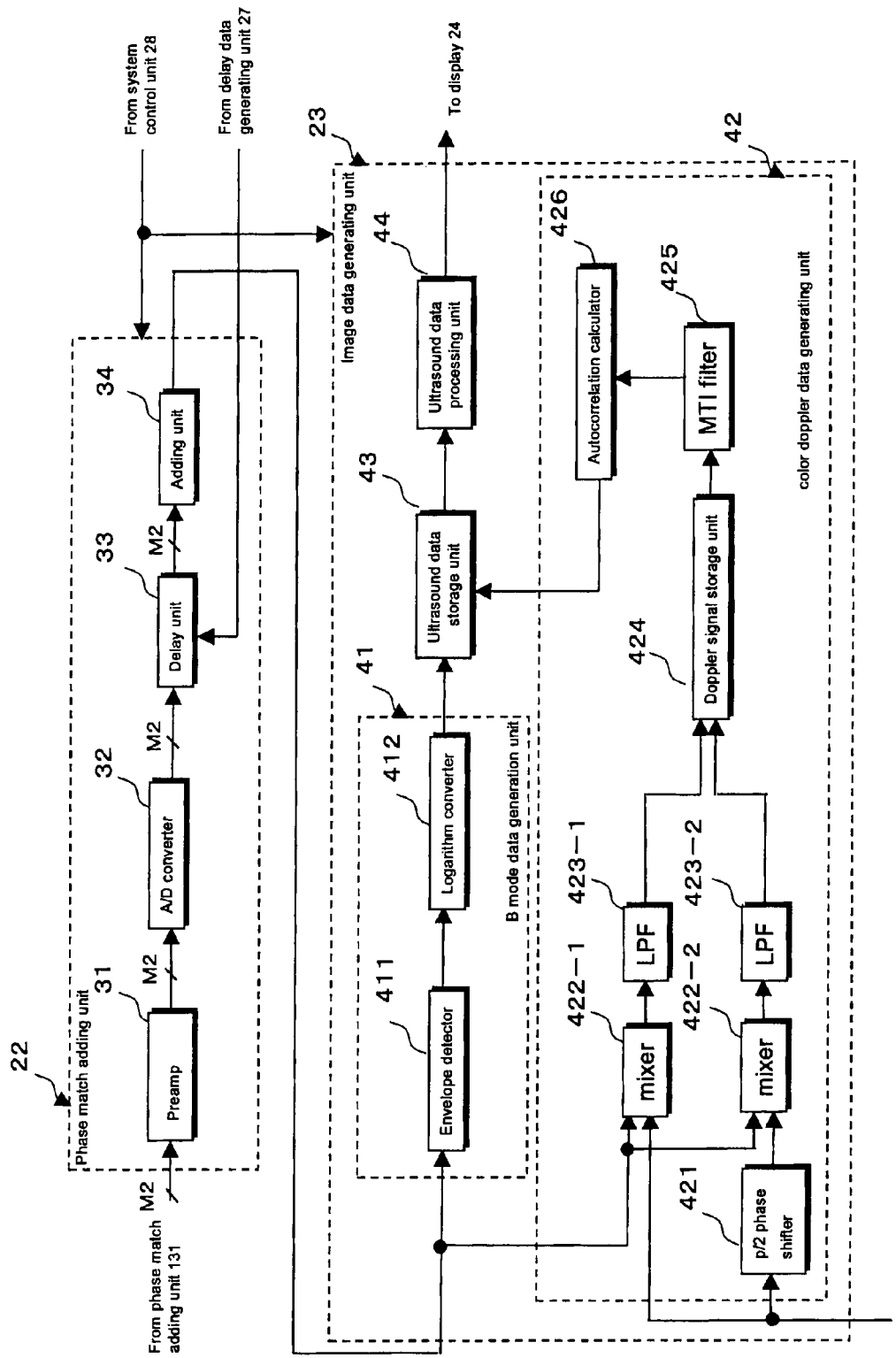
FIG. 6 is a block diagram showing components of a second phase match adding unit and an image data generating unit of an exemplary embodiment of the ultrasound diagnostic apparatus of the invention.

Next, a concrete example of the second phase match adding unit 22 and image data generating unit 23 is explained with the reference to the block diagram shown in FIG. 6. The second phase match adding unit 22 includes a preamp 31, an A/D converter 32, a delay circuit 33 and an adding circuit 34. The preamp 31 amplifiers the M2 channel receiving signal supplied from the first phase match adding units 131-1 to 131-M2 of the ultrasound probe 1 via a cable so that enough S/N is acquired. The amplified receiving signal is converted into digital signal at the A/D converter 32 and transmitted to the delay unit 33.

The delay circuit 33 delays the digital converted signal so that the added signal has directivity and is focused at a predetermined depth. The delayed received signals are added in the adding circuit 34. In other words, M1 channel receiving signals supplied from receiving unit 13 of ultrasound probe 1 are phase matched and added into a 1 channel receiving signal by the delay circuit 33 and the adding circuit.

The number of channels of the signal cable is decreased because the phase match adding unit 131-1 to 131-M2 in the ultrasound probe 1 and the second matching and adding unit 22 in the apparatus body 2 shares adding of receiving signals. This method is described in above mentioned Japanese patent disclosure (kokai) No 2005-342194 particularly.

The ultrasound data processing unit 23 shown in FIG. 5 includes a B mode data generation unit 41, a color Doppler data generation unit 42, an ultrasound data storage unit 43, and an ultrasound data processing unit 44.

The B mode data generation unit 41 includes an envelope detector 411 which calculate the envelope curve of the complex received signals supplied from the adding unit 34 of the second phase match adding unit 22 and a logarithm converter 412 which converts the detected envelope curve to B mode data.

The color Doppler data generation unit 42 includes $\pi/2$ phase shifter 421, mixer 421-1 and 422-2 and LPF (low pass filter) 423-1 and 423-2. The color Doppler data generation unit 42 processes longitudinal phase detection the received signal supplied from adding unit 34 and generates complex received signals (I signal and Q signal).

The color Doppler data generation unit 42 further includes a Doppler signal memory 424 which stores the complex received signal, an MTI filter 425 which removes clutter signal caused from whole movement of the subject and an autocorrelation calculator 426 which calculates autocorrelation between sets of the filtered received signals stored in the Doppler signal memory 424 and generates color Doppler data indicating the velocity of blood.

Next, the ultrasound data storage unit 43 sequentially stores ultrasound data of a 2-dimensional region or a 3-dimensional region generated by the B mode data generating 41 unit and the color Doppler data generating unit 42. The ultrasound data generation unit 44 processes 3-dimensionally data stored in the ultrasound data storage unit and generates 2-dimensional data, which is volume rendering image data, surface rendering data, MIP (maximum intensity projection) image data. The ultrasound data processing unit 44 may also generate image data that is filtered or edge enhanced.

Returning to FIG. 1, the display unit 24 includes a not shown display data generation unit, conversion unit and monitor. The display data generation unit generates data for display from 3-dimensional image data or 2-dimensional image data generated by ultrasound image data generating unit 23. The generation of the data for display is executed by scan conversion in accordance with a predetermined format of display. The conversion unit executes a D/A conversion of the supplied data for display and TV format conversion. The monitor displays the data converted by the conversion unit.

The input unit 25 includes an operation panel which has a display panel, a key board, a track ball, a mouse, a selection button, input button and so on provided thereon. An operator inputs information of the subject, acquiring conditions for volume data, display conditions or some kind of command signal.

Next, the scan control unit 26 sets transmitting and receiving direction of 3-dimensional scan or 2-dimensional scan on the basis of imaging condition supplied from the input device 25 via the system control unit 28. Furthermore, the delay data generating unit 27 generates delay data for setting of phase delay or time delay for the first phase match adding unit 131-1 to 131-M2 and the second phase match adding unit 22 on the basis of information of the setting of the second oscillation element group, the imaging condition and the transmitting and receiving directions, or may extract delay data from stored kinds of delay data in the not shown delay data storage unit for the first phase match adding unit 131-1 to 131-M2 and the second phase match adding unit 22.

Furthermore, the system control unit 28 includes a not shown CPU and a memory. The information inputted from the input unit 25 by the operator is stored in the memory. The CPU wholly controls each unit mentioned above on the basis of the stored information.

In the above mentioned exemplary embodiment of the present invention, the common delay setting of the second oscillation element group enables a decrease in the amount of delay data to be supplied to the ultrasound probe 1. Therefore, the transfer time of the delay data is shortened. In the other words, amelioration of time resolution and power consumption is achieved without deterioration of image quality of the image data by setting the second oscillation element group according to needed accuracy of delay data.

Especially, in the case that frequency of transmitting ultrasound wave is low and that scan range is narrow, the time resolution of image data acquisition is ameliorated. Furthermore, high time resolution color Doppler image data and high space resolution B mode image data are acquired at the same time.

In addition, in the above mentioned exemplary embodiment, because common phase delay is gave the received signal from oscillation element belonging to the second oscillation element group, the first phase match adding unit can be composed of simple circuitry.

For example, in the case where it is simply desired to decrease transfer time of delay data by common connection of oscillation elements to be given same delay data to, switch circuits are needed for all the oscillation elements. On the other hand, in this exemplary first oscillation embodiment, common phase delay is given to the first phase match adding unit for the first oscillation element group in the ultrasound probe. Therefore, this method can be adopted in the technique disclosed in the Japanese patent disclosure (kokai) 2005-343294. This exemplary embodiment decreases transfer time without change of above mentioned formerly known circuit components.

Numerous variations of the present invention are possible in light of the above description. It is therefore to be understood that the invention as claimed can be practiced other than is specifically described herein.

For example, common delay setting may be applied not only received signals but also to driving signals for the M0 oscillation elements. In one example of this technique, the transmitting delay setting unit 121 in the transmitting part 12 shown in FIG. 1 may divide the oscillation elements into third oscillation element groups on the basis of information of imaging condition(s) supplied from the system control unit 28. Next, in accordance with delay data generated by the delay data generation unit 27 on the basis of the dividing information, the transmitting delay setting unit 121 may set a common delay to driving signals for oscillation element belonging to one third oscillation element group.

However, the case that the common delay is only set for receiving signals is more effective to maintain image quality compared to the case that common delay setting is not adopted. When receiving signals are phase matched and added, normally, an A/D converter is provided. Because the accuracy of the A/D converter is limited, the required accuracy of the receiving delay is more flexible than the transmitting delay.

In addition, the above mentioned technique can be adopted not only to 2-dimensional allayed probe but also to 1-dimension arrayed probe. In the case of 1-dimension arrayed probe, the same effect as is the case of 2-dimensional arrayed probe can be obtained.

Furthermore, in above mentioned exemplary embodiment, second oscillation element groups are set for every scan region. In other words, setting of the second oscillation element groups is changed between an end portion and a center portion while one frame region is scanned. However, such frequent changing may not be executed and setting of the second oscillation element groups may be fixedly set in accordance with the width of whole scan region (field angle).

In addition, in above mentioned exemplary embodiments settings of the second oscillation element groups are same in the every first oscillation element group. However, when transmitting and receiving is executed for one scan line of a scan region, fine division of the second oscillation element groups for one first oscillation element group, where the difference in delay between oscillation elements is large and coarse division of the second oscillation element groups for one first oscillation element group where difference of delay between oscillation elements is small, may be set at the same time.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound diagnostic apparatus, comprising:
an ultrasound probe including oscillation elements configured to transmit toward and receive from a region of a subject;
a receiving delay setting unit configured to divide the oscillation elements into first oscillation element groups, to determine a number of oscillation elements belonging to each of second oscillation element groups in accordance with an imaging condition, to divide each of the first oscillation element groups into the second oscillation element groups in accordance with the determined number of the oscillation elements, and to set a common delay to the oscillation elements included in each of the second oscillation element groups;
an adding unit including a first adding unit and a second adding unit, wherein the first adding unit is configured to add received signals of plural channels transmitted from the oscillation elements belonging to each of the first oscillation element groups, wherein the second adding unit is configured to further add received signals of the plural channels added by the first adding unit; and
an image generating unit configured to generate image data in accordance with the received signals added by the adding unit.

2. The ultrasound diagnostic apparatus according to claim 1, wherein
the first adding unit is provided in the ultrasound probe; and
the second adding unit is provided in an apparatus body external to said ultrasound probe.

3. The ultrasound diagnostic apparatus according to claim 1, wherein the imaging condition is one of an imaging mode, a frequency of transmitting an ultrasound wave, a scan line density, and a scan region.

4. The ultrasound diagnostic apparatus according to claim 2, wherein the first adding unit sets a common phase delay or a time delay to oscillation elements included in each of the first oscillation element groups.

5. The ultrasound diagnostic apparatus according to claim 4, further comprising:
a delay data generating unit configured to generate delay data corresponding to the phase delay or the time delay, wherein the receiving delay setting unit commonly sets the delay data for each of the first oscillation element groups corresponding to oscillation elements belonging to each of the second oscillation element groups.

6. The ultrasound diagnostic apparatus according to claim 5, further comprising:
a scan control unit configured to control a direction of ultrasound transmitting and receiving,
wherein the delay data generation unit generates delay data in accordance with information of the direction of ultrasound transmitting and receiving and a division of the second oscillation element groups.

7. The ultrasound diagnostic according to claim 5, wherein the delay data generating unit is configured to sequentially supply the delay data to the receiving delay setting unit.

8. The ultrasound diagnostic apparatus according to claim 7, wherein the delay data generating unit is provided in the apparatus body and the receiving delay setting unit is provided in the ultrasound probe.

9. The ultrasound diagnostic apparatus according to claim 1, further comprising:
a driving unit configured to supply driving signals to the oscillation elements; and
a transmitting delay setting unit configured to divide the oscillation elements into third oscillation element groups and to set a common delay to oscillation elements included in each of the third oscillation element groups in accordance with an imaging condition for the driving signals.

10. The ultrasound diagnostic apparatus according to claim 1, wherein the oscillation elements are arrayed 2-dimensionally.

11. A method of acquiring ultrasound data, comprising:
transmitting toward and receiving ultrasound signals from a region of a subject using oscillation elements provided in an ultrasound probe;
dividing the oscillation elements into first oscillation element groups;
determining a number of oscillation elements belonging to each of second oscillation element groups in accordance with an imaging condition;
dividing each of the first oscillation element groups into the second oscillation element groups in accordance with the determined number of the oscillation elements;
setting a common delay to oscillation elements included in each of the second oscillation element groups;
first adding received signals of a plurality of channels transmitted from the oscillation elements belonging to each of the first oscillation element groups in accordance with the common delay;
second adding received signals of the plurality of channels added in the first adding step; and
generating image data in accordance with the received signal added by the adding unit.

12. The method of acquiring ultrasound data according to claim 11, wherein
the first adding step is performed in the ultrasound probe, and
the second adding step is performed in an apparatus body provided external to the ultrasound probe.

13. The method of acquiring ultrasound data according to claim 11, wherein the imaging condition is one of an imaging mode, a frequency of transmitting an ultrasound wave, a scan line density, and a scan region.

14. The method of acquiring ultrasound data according to claim 11, wherein the setting step comprises setting a common phase delay or a time delay to oscillation elements included in each of the first oscillation element groups.

15. The method of acquiring ultrasound data according to claim 14, further comprising:
generating delay data corresponding to the phase delay or the time delay; and
the setting step includes commonly setting the delay data for the first adding step corresponding to oscillation elements belonging to each of the second oscillation element groups.

16. The method of acquiring ultrasound data according to claim 15, further comprising:
controlling a direction of ultrasound transmitting and receiving,
wherein the generating step comprises generating the delay data in accordance with the direction of ultrasound transmitting and receiving and the division of the second oscillation element groups.

17. The method of acquiring ultrasound data according to claim 15, wherein the generating step comprises supplying the delay data sequentially.

18. The method of acquiring ultrasound data according to claim 17, wherein the generating step is executed in the apparatus body and the setting step is executed in the ultrasound probe.

19. The method of acquiring ultrasound data according to claim 11, further comprising:
supplying driving signals to the oscillation elements;
dividing the oscillation elements into transmitting oscillation element groups; and
setting a common delay to oscillation elements included in each of the transmitting oscillation element groups in accordance with an imaging condition for the driving signals.

20. The method of acquiring ultrasound data according to claim 11, wherein the oscillation elements are arrayed 2-dimensionally.

* * * * *